United States Patent [19]

Greener

[11] 3,997,328
[45] Dec. 14, 1976

[54] DENTAL AMALGAMS

[75] Inventor: Evan H. Greener, Elk Grove Village, Ill.

[73] Assignee: Engelhard Minerals & Chemicals Corporation, Murray Hill, N.J.

[22] Filed: Dec. 29, 1975

[21] Appl. No.: 644,870

[52] U.S. Cl. .......................... 75/0.5 R; 75/134 N; 75/169; 75/173 C
[51] Int. Cl.² .......................................... C22C 7/00
[58] Field of Search ............ 75/.5 R, 173 C, 173 R, 75/134 N, 134 C, 169

[56] References Cited

UNITED STATES PATENTS

| | | | |
|---|---|---|---|
| 1,963,085 | 6/1934 | Gray | 75/173 C |
| 2,281,991 | 5/1942 | Poetschke | 75/173 C |
| 3,305,356 | 2/1967 | Youdelis | 75/173 C X |
| 3,841,860 | 10/1974 | Wolf | 75/.5 R |
| 3,871,876 | 3/1975 | Asgar et al. | 75/169 |
| 3,933,961 | 1/1976 | Burns | 75/169 X |
| 3,954,457 | 5/1976 | Weikel | 75/169 |

Primary Examiner—L. Dewayne Rutledge
Assistant Examiner—E. L. Weise

[57] ABSTRACT

Dental compositions comprising an admixture of two powdered alloys which when amalgamated with mercury produce corrosion-resistant dental amalgams.

8 Claims, 1 Drawing Figure

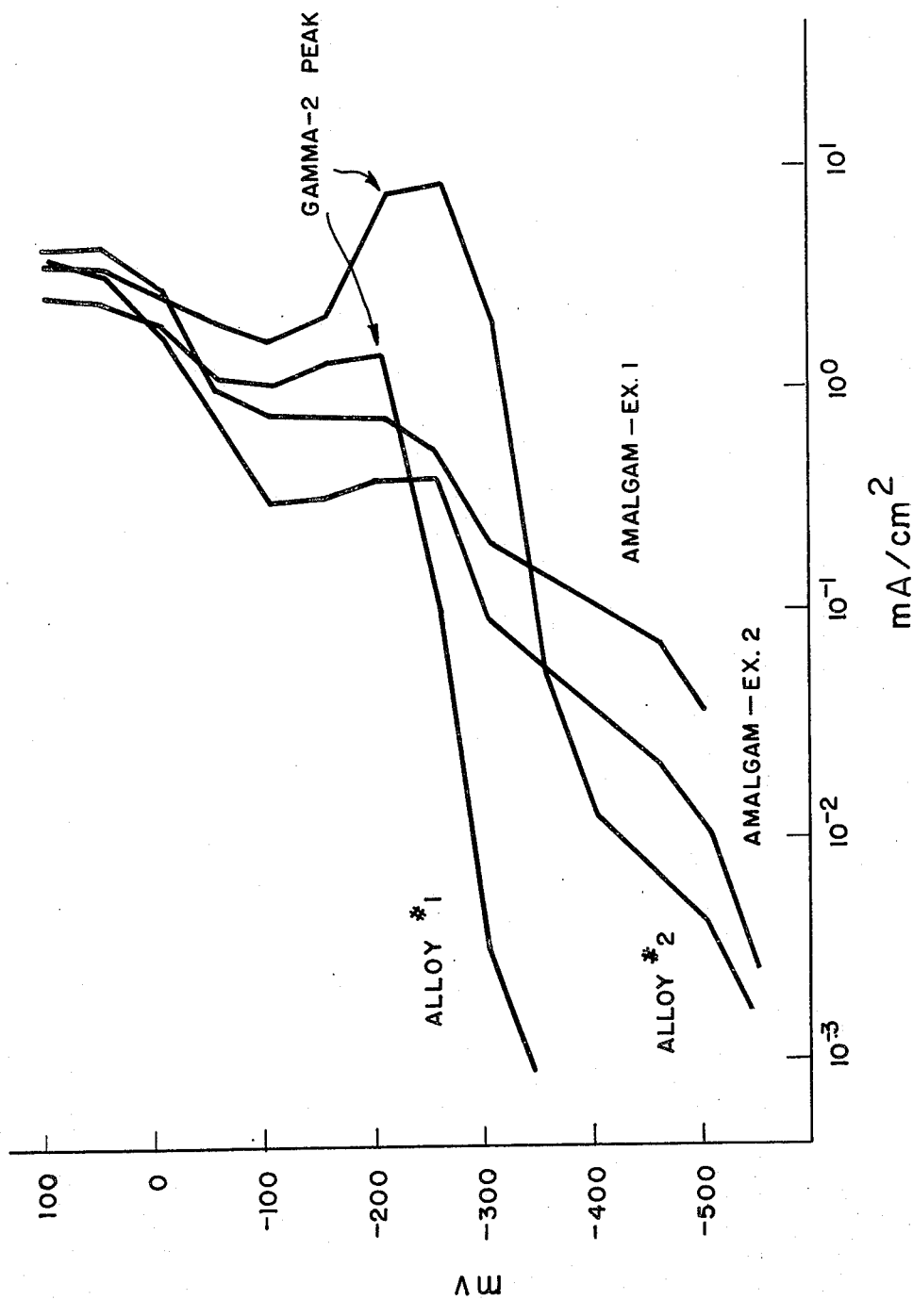

DENTAL AMALGAMS

This invention relates to new dental amalgam compositions and to their preparation. More specifically, it relates to a uniform admixture of specified proportions of two powdered alloys of specific composition which when amalgamated with mercury exhibit enhanced corrosion resistance.

BACKGROUND

Dental amalgams are produced by intimately combining mercury with dental amalgam alloys, conventional of which are comprised generally of from about 67-72% by weight of silver, 25-27% tin, 0-5% copper and 0-2% zinc. Upon reaction with mercury using known dental clinical techniques, a plastic mass is produced which quickly sets into a hard rigid body. While the mass is plastic, it may be packed into a surgically prepared tooth restoring its anatomy and function.

The products of the amalgamation reaction are believed to be a silver-mercury reaction product ($Ag_2Hg_3$) and a tin-mercury reaction product ($Sn_{7-8}Hg$), referred to in the art as gamma-1 and gamma-2, respectively. It has been recognized that the presence of gamma-2 in dental amalgams is a source of corrosion in a saline environment. It is believed that the corrosion process probably releases mercury as a reaction product, resulting in the undesired formation of additional voids and porosities. These may extend well below the surface since the gamma-2 phase in dental amalgam is interconnected. The excess mercury, voids and porosities serve to weaken the dental amalgam especially at the margins which are the interfaces between the restoration and tooth. As a consequence of normal occlusion, stresses generated at a weakened margin may destroy its integrity, allowing leakage of oral fluids and bacteria, thereby promoting secondary decay.

Regardless of whether the aforementioned explanation of the corrosion process due to the presence of gamma-2 is correct (and the present invention is not necessarily limited thereto), it has been found that corrosion can be reduced by techniques which minimize, inhibit or eliminate gamma-2 from dental amalgam compositions. U.S. Pat. No. 3,305,356, for example, discloses the preparation of dental amalgams by mechanically dispersing a hard, strong metal alloy comprising copper and silver throughout a conventional amalgam in the form of very fine particles. There is evidence that in such compositions some of the copper from the dispersed silvercopper alloy combines with tin, thereby inhibiting gamma-2 formation. This is not effective immediately, however, since the copper must first diffuse through a reaction zone which forms around the dispersant. From a corrosion standpoint the gamma-2 is eliminated over a period of weeks after initial trituration and condensation.

Inhibition of gamma-2 has also been attempted by use of silver-tin alloys containing about 5% gold. While the formation of gamma-2 may be somewhat inhibited in such alloys, the resulting gold-tin phase that forms is also subject to saline corrosion. Moreover, the amount of gold required to eliminate gamma-2 completely makes such dental amalgams expensive.

Similarly, for a number of years some dentists have been adding empirical amounts of copper-mercury (copper amalgam) to already triturated conventional amalgam. This procedure produces a good clinical amalgam the structure of which appears to contain little or no gamma-2 phase immediately after trituration. The disadvantage of this technique is that the copper amalgam is heated until mercury beads at its surface prior to mixing. This presents a substantial mercury hazard to the dental personnel and perhaps to the patient.

Other approaches, which may employ high copper content compositions, are disclosed, for example, in U.S. Pat. Nos. 2,281,991 and 3,871,876. In the former a mixture of two comminuted alloys are employed, one, however, being a preformed hardened silver amalgam rich in silver and mercury, which requires special handling procedures. In the latter, advantageous results are reported for an amalgamable silver alloy powder, wherein the particles are generally spheroidal and each particle has a gradient composition from exterior to interior, a characteristic requiring special manufacturing techniques.

Still other approaches have met with some success in minimizing or eliminating the gamma-2 phase, but with undesired side effects. For example, some otherwise successful compositions require increased amounts of mercury for amalgamation of the alloy.

OBJECTS OF THE INVENTION

It is a general object of this invention to provide dental amalgam compositions which cope with the aforementioned problems of other amalgams.

It is a specific object to provide high-copper-content dental amalgamable compositions which are substantially free of mercury prior to amalgamation and which can be readily amalgamated without undue risks to personnel resulting from excessive mercury exposure.

It is another specific object to provide new dental amalgam compositions which upon amalgamation with mercury do not unduly form the gamma-2 phase and which provide enhanced electrochemical properties.

It is another specific object to provide dental amalgam compositions which upon amalgamation with mercury substantially immediately inhibit gamma-2 formation so as to be substantially free of the gamma-2 phase and yet are competitive in cost with other amalgam compositions.

It is another specific object to provide an amalgamable dental composition which can be prepared or manufactured employing conventional techniques.

It is another specific object to provide dental amalgam compositions having improved properties upon amalgamation without unduly increasing the amounts of mercury required in the preparation thereof.

These and other objects will become apparent as the detailed description proceeds.

DESCRIPTION OF THE INVENTION

The new and improved dental amalgam compositions of this invention comprise an admixture of two alloys, hereinafter referred to as Alloy No. 1 and Alloy No. 2, respectively, in comminuted or powdered form, the proportions of the two alloys being somewhat critical for optimum results. Alloy No. 1 as employed in this invention is comprised of silver, tin and copper with silver present in the range of about 40 to 70% by weight, tin in the range of about 10 to 30% by weight and copper in the range of about 20 to 40% by weight. Alloy No. 2 used in accordance with the invention is comprised of silver tin, copper and zinc with silver present in the range of about 55 to 70% by weight, tin in the range of about 20 to 40% by weight, copper in the range of about 0.05 to 10% by weight of zinc in the range of about 0.1 to 2.0% by weight.

Alloy No. 1 is preferably present as a major proportion of the composition, i.e., more than about 50% by weight, e.g., about 55 to about 90% of the composition by weight, optimally about 70 to about 80%, whereas Alloy No. 2 is preferably present as a minor proportion, i.e., less than about 50% by weight, e.g., about 10 to about 45% by weight, optimally about 20 to about 30%. In an optimal case, the powdered alloys are present in the proportion of about 3 parts of Alloy No. 1 and about 1 part of Alloy No. 2 by weight. Thus, for 100 parts of a complete dental amalgam composition, approximately 75 parts of Alloy No. 1 are mixed with approximately 25 parts of Alloy No. 2.

To form a dental amalgam composition in accordance with this invention Alloy No. 1 and Alloy No. 2, both in powdered or particulate form, are mechanically or manually mixed to produce a substantially uniform blend. In the preferred mechanical embodiment, the two alloys are mechanically mixed in a conventional blender for at least about 15 minutes, e.g., about ½ hour to about 1½ hours, typically about 1 hour.

The particle size distribution of both Alloy No. 1 and Alloy No. 2 is normally within the range of about 1 to about 100 microns, e.g., about 2 to about 80 microns, preferably about 5 to about 40 microns. The particle size range designation means that substantially all of the particles will pass a sieve or screen having openings corresponding to the larger size and substantially all of the particles will be retained on a sieve or screen having openings corresponding to the smaller size. The average particle size is typically in the range of about 20 to 30 microns.

The particles of both alloys are typically in the form of what is variously referred to as microcut material, lathe-cut material, platelets or filings so that the particles are generally of non-smooth irregular shape. Conventional microcutting, lathe cutting or filing techniques can be employed satisfactorily to obtain the irregularly shaped particles and are well known to those skilled in the art.

For dental use, the complete amalgam composition is triturated with mercury which is used in amounts of from about 0.8:1 up to about 1.5:1 parts of mercury by weight per part of the alloy powder. Preferably mercury is employed in a ratio of from about 0.9:1 to about 1.4:1 parts of mercury by weight, per part of alloy powder, optimally about 1:1.

Conventional trituration equipment and techniques may be employed, such as the condensation technique of the American Dental Association Specification No. 1 for dental amalgams. Typically, a one-spill trituration time of about 3–8 seconds at a vibration frequency of about 3,000 to 4,000 cycles per minute may be employed, e.g., about 5 seconds at about 3,500 cycles per minute.

DESCRIPTION OF THE DRAWING

The present invention will be more clearly understood from the accompanying drawing wherein FIG. 1 shows the anodic polarization diagrams for specific embodiments of Alloy No. 1 by itself and Alloy No. 2 by itself, as well as for blended amalgams of the present invention prepared therefrom, as set forth in Examples 1 and 2 hereinafter. These diagrams represent one means of detecting the presence of gamma-2, as more fully described hereinafter.

The following examples further illustrate the present invention or provide comparative information and data which point up the advantages of the present invention.

EXAMPLE 1

A particularly preferred dental composition was produced by mechanically mixing 3 parts by weight of an alloy (Alloy No. 1) comprised of 50% by weight silver, 30% by weight copper and 20% by weight of tin with 1 part by weight of an alloy (Alloy No. 2) comprised of 68% by weight silver, 27% by weight tin, 4.4% by weight copper and 0.6% by weight zinc. Both of the alloys were composed of irregularly shaped particles in the range of 5 to 40 microns. Mechanical mixing of the powdered alloys was conducted to provide a substantially uniform blend. The resulting powdered dental composition was triturated in conventional manner with mercury using the condensation technique of the American Dental Association Specification No. 1 for dental amalgams. Seven parts of mercury were used with 5 parts of the powdered alloy mixture to produce a dental amalgam.

EXAMPLE 2

For comparative purposes, the procedure of Example 1 was repeated with the exception that the same two alloys were mixed in a part ratio of 1:1. The resulting powdered dental composition was triturated in conventional manner with mercury using the condensation technique of the American Dental Association Specification No. 1 for dental amalgams. Seven parts of mercury were used with 5 parts of the powdered alloy mixture to produce a dental amalgam.

EXAMPLE 3

For comparative purposes, the procedure of Example 1 was repeated with the exception that the same two alloys were mixed in a part ratio of 5 parts of Alloy No. 1 to 1 part of Alloy No. 2. The resulting powdered dental composition was triturated in conventional manner with mercury using the condensation technique of the American Dental Association Specification No. 1 for dental amalgams. Seven parts of mercury were used with 5 parts of the powdered alloy mixture to produce a dental amalgam.

EXAMPLE 4

For comparative purposes, the alloy mixture of Example 1 was melted to form a single alloy rather than an admixture of the two powdered alloys, the resulting single alloy then being comminuted so as to form a powder of irregularly shaped particles having approximately the same irregularly shaped particles and particle-size distribution as in Example 1. The resulting melted alloy mixture in powdered form was triturated in conventional manner with mercury using the condensation technique of the American Dental Association Specification No. 1 for dental amalgams. Eight parts of mercury with 5 parts of the alloy were required to produce a workable dental amalgam.

The dental amalgams of Examples 1, 2, 3 and 4 were subjected to tests to determine compressive strength, diametral tensile strength, flow characteristics and dimensional change. The results of the tests are tabulated in following Table I:

Table I

| Example | Compressive Strength, psi After 48 Hrs. | Diametral Tensile Strength, psi After 15 Min. | Diametral Tensile Strength, psi After 24 Hrs. | Flow Test, % | Dimension Change Test, %/cm |
|---|---|---|---|---|---|
| 1 | 51,925 | 710 | 5,256 | 0.5 | +0.01 |
| 2 | 65,600 | 591 | 6,257 | — | 0 |
| 3 | — | 547 | 3,880 | 1.7 | +0.03 |
| 4 | 33,500 | 318 | 3,540 | 0.9 | 0 |

The amalgams of Examples 1 and 2 and also the amalgams made from Alloy No. 1 by itself and Alloy No. 2 by itself were checked for the presence of gamma-2. This was done by anodic polarization measurements in saline solution for about 24 hours after trituration and condensation, the results being presented in the anodic polarization diagrams shown in FIG. 1. As already mentioned, these diagrams represent one means of detecting the present of gamma-2, the indication being a current density peak at about −250 mv(SCE), indicative of the formation of tin oxide or tin oxychloride. The technique is at least as sensitive as X-ray diffraction for detection of the gamma-2 phase and is further described in the literature, e.g., Journal of Dental Research, Vol. 51, No. 6, November—December 1972, at page 1675 (Copyright 1972 by International Association for Dental Research).

As shown in FIG. 1, the amalgams of Examples 1 and 2 do not display the peak associated with the presence of gamma-2 and their electrical current densities are lower than the densities obtained with Alloy No. 1 by itself or Alloy No. 2 by itself in the unmixed state. The absence of the gamma-2 peak is indicative of resistance to gamma-2 corrosion. It is evident from Table I that the amalgams of Examples 1 and 2 have satisfactory physical properties.

It will be noted that when the physical properties shown in Table I and the corrosion resistant properties are considered collectively, optimum results were achieved by an admixture of the two alloys described herein in a ratio of 3:1, as employed in Example 1. With such preferred compositions dental amalgam compositions are obtained which not only have desired corrosion resistance but also meet the specifications established by the American Dental Association.

It will also be noted that while the mixture of Example 4 has the same chemical composition and particle size distribution as the preferred mixture of Example 1, it required a higher mercury-alloy ratio to produce a workable dental amalgam. In addition, it was distinctly inferior with respect to physical properties.

Further illustrative examples are as follows:

EXAMPLE 5

An amalgamable dental composition in accordance with the invention is prepared by mechanically mixing 4 parts of an alloy composed of 60% by weight silver, 15% by weight tin and 25% by weight copper with 2 parts of an alloy composed of 60% by weight silver, 32% by weight tin, 7% by weight copper and 1% by weight zinc. Both of the alloys are composed of irregularly shaped particles having a particle size distribution within the range of about 5 to 40 microns.

EXAMPLE 6

An amalgamable dental composition in accordance with the invention is prepared by mechanically mixing 4 parts of an alloy composed of 55% by weight silver, 18% by weight tin and 27% by weight copper with 1 part of an alloy composed of 64% by weight silver, 29% by weight tin, 4.5% by weight copper and 0.5% by weight zinc. Both of the alloys are composed of irregularly shaped particles having a particle size distribution within the range of about 5 to 40 microns.

EXAMPLE 7

An amalgamable dental composition in accordance with the invention is prepared by mechanically mixing 3 parts of an alloy composed of 45% by weight silver, 22% by weight tin and 33% by weight copper with 2 parts of an alloy composed of 62% by weight silver, 33% by weight tin, 4.2% by weight copper and 0.8% by weight zinc. Both of the alloys are composed of irregularly shaped particles having a particle size distribution within the range of about 5 to 40 microns.

While it is essential that the dental composition of this invention be in the form of a mixture of particulates of the two alloys when used, and may be supplied in such form when supplied, it should be understood that for distribution purposes the two alloys can be in the form of separate powders which can be admixed by the ultimate user in the required proportions. Alternatively, the two admixed alloys in the required proportions can be pressed into tablet or capsule form for convenience.

While only certain embodiments have been set forth, alternative embodiments and various modifications of the embodiments depicted will be apparent from the above description to those skilled in the art. These and other alternatives are considered equivalents and within the spirit and scope of the present invention.

Having described the invention, what is claimed is:

1. A composition adapted for amalgamation with mercury to form a dental amalgam consisting essentially of a uniform admixture of a major proportion of a first alloy composed of about 40 to 70% by weight silver, about 10 to 30% by weight tin and about 20 to 40% by weight copper in particulate form, and a minor proportion of a second alloy composed of about 55 to 75% by weight silver, about 20 to 40% by weight tin, about 0.05 to 10% by weight copper and about 0.1 to 2.0% by weight zinc in particulate form.

2. A composition of claim 1 wherein both of the alloys are in the form of irregularly shaped particles.

3. The composition of claim 1 wherein both of the alloys have a particle size distribution in the range of about 1 to about 100 microns.

4. The composition of claim 1 containing about 55 to about 90% by weight of said first alloy and about 10 to about 45% by weight of said second alloy.

5. The composition of claim 1 wherein approximately 3 parts by weight of said first alloy are employed per 1 part by weight of said second alloy.

6. A process for preparing a dental amalgam which comprises triturating the composition of claim 1 with sufficient mercury to form a workable plastic amalgam.

7. A composition adapted for amalgamation with mercury to form a dental amalgam comprising a substantially uniform blend of:
   a. about 55 to 95% by weight of a first powder having a particle size distribution in the range of about 1 to 100 microns and consisting essentially of an alloy of about 40 to 70% by weight silver, about 10 to 30% by weight tin and about 20 to 40% by weight copper; and
   b. about 5 to 45% by weight of a second powder having a particle size distribution in the range of about 1 to 100 microns and consisting essentially of an alloy of about 55 to 75% by weight silver, about 20 to 40% tin, about 0.05 to 10% by weight copper and about 0.1 to 2.0% by weight zinc.

8. A process for preparing a dental amalgam which comprises triturating the composition of claim 7 with mercury in the proportion of about 0.8 to about 1.5 parts by weight of mercury per part by weight of said composition to form a workable plastic amalgam.

* * * * *